United States Patent [19]

Rehme et al.

[11] 4,351,190

[45] Sep. 28, 1982

[54] ULTRASONIC NON-DESTRUCTIVE TESTING DEVICE FOR WELDING BEADS

[76] Inventors: Wilfried Rehme, Brunnenweg 11, D-5200 Siegburg-Braschoss, Fed. Rep. of Germany; Anatoly Stipura, Ul Kirova 9; Victor Ripnyi, Pr Pravdi 113, both of Dnepropetrovsk, U.S.S.R.; Leonid Donskoi, Ul Argunovskaja 12; Nikolai Schevtschenko, Pr Mira 188, both of Moscow, U.S.S.R.

[21] Appl. No.: 231,134
[22] PCT Filed: Sep. 11, 1979
[86] PCT No.: PCT/DE79/00105
§ 371 Date: May 13, 1980
§ 102(e) Date: May 13, 1980
[87] PCT Pub. No.: WO80/00616
PCT Pub. Date: Apr. 3, 1980

[51] Int. Cl.³ .............................................. G01N 29/04
[52] U.S. Cl. ...................................... 73/638; 73/622
[58] Field of Search ................. 73/638, 640, 622, 625, 73/588

[56] References Cited

U.S. PATENT DOCUMENTS 3,350,925 11/1967 Coy ........................................ 73/638
3,868,847 3/1975 Gunkel ................................. 73/622

FOREIGN PATENT DOCUMENTS 2751810 5/1979 Fed. Rep. of Germany .
2840456 3/1980 Fed. Rep. of Germany ........ 73/638
2295422 7/1976 France .

Primary Examiner—Anthony V. Ciarlante
Attorney, Agent, or Firm—Meyer, Tilberry & Body

[57] ABSTRACT

An ultrasonic non-destructive testing device for welded seams on pipes and tubes comprises two test heads arranged opposite one another on a line normal to the welded seam. Each test head comprises a transducer element for longitudinal defects and two transducer elements for transverse defects. The transducer elements for transverse defects interact with transducer elements on the opposite side of the welded seam. The device allows the complete automatic testing of a welded seam from the beginning of the pipe to the end of the pipe for longitudinal and transverse defects.

6 Claims, 3 Drawing Figures

ULTRASONIC NON-DESTRUCTIVE TESTING DEVICE FOR WELDING BEADS

BACKGROUND OF THE INVENTION

The invention relates to ultrasonic non-destructive testing devices for weld beads, particularly on pipes or tubes with a straight or helical welded seam.

In the testing of welded seams of tubes or pipes, particularly of large tubes with longitudinal or helical seams produced by submerged arc welding, ultrasonic testing devices with several testing heads are used which examine the welded seam for longitudinal and transverse defects. Longitudinal defects are faulty spots which extend in the longitudinal direction of the welded seam, for instance slag inclusions or air pockets. Transverse defects are defects which extend at right angles to the axis of the welded seam. In current testing devices various kinds of testing heads are used. Standard and angle testing heads have only one test transducer which transmits its sonic rays perpendicularly or at an acute angle to the welding seam. Double angle testing heads have two angularly arranged test transducers, one of which serves for the detection of longitudinal defects and the other for the detection of transverse defects. Alternate double angle testing heads use one transducer and a device which splits off a portion of the sonic rays and directs the split rays at an angle to the welded seam in order to detect longitudinal defects and transverse defects. Of course, these transducers also receive the sonic rays transmitted through the tube under test and converts them to electrical signals for processing.

In a known testing device four standard or angle testing heads are symmetrically arranged with respect to the seam in a K- or X-shaped arrangement. The four testing heads form a test spider which is set upon the tube and guided along the welded seam. The sound-transmitting coupling is achieved between the transducers and the tube by the supply of water into the space between the tube and these transducers. The coupling between the transducers and the tube is monitored by ultrasonic means with special control transducers in order to detect possible coupling faults such as air bubbles or loose slag.

In operation the testing heads are connected to a programmed ultrasonic impulse source and evaluating electronics. Longitudinal and transverse reflex testing beats are directed to the various transducers and appropriate receiving transducers are interrogated individually or in pairs.

In another known construction two double-angle testing heads lying on opposite sides of the welded seam opposite each other are used. Each testing head emits two sonic rays split off at 45° by a quartz crystal. The ultrasonic rays which hit the welded seam perpendicularly to its longitudinal direction detect longitudinal defects and the ultrasonic rays which hit the welded seam at an angle of 45° detect transverse defects.

All known devices have the characteristic that a complete examination for longitudinal and transverse defects is possible only when all testing heads are set upon the tube. The examination is therefore satisfactory in the mid-range of a tube, but fails at the beginning or at the end of the tube. When the tube is just slipped under the test spider or withdrawn from it and two of the testing heads in a K- or X- arrangement do not yet lie or no longer on the tube coupling in not present and testing cannot be performed.

This peculiarity leads to the disadvantage that the area of the welded seam at the beginning or at the end of the tube cannot be completely examined for longitudinal and transverse defects. These unexamined areas can be up to 20 centimeters (7.8 inches) in length. It was therefore always necessary to examine these unexamined areas of the welded seam at the beginning and the end of the tube manually with hand-operated ultrasonic instrucments. Manual examination requires a considerable expenditure with regard to technology and personnel.

In an older testing device of the applicant not belonging to the state of technology test transducers for the recognition of longitudinal and transverse defects are accommodated in testing heads which are arranged in a star-like test spider disposed symmetrically with respect to the welded seam. It is possible to examine welded seams for longitudinal and transverse defects with this device completely from beginning to end in a fully automatic manner. However, at least six testing heads are required for the complete examination of the welded seam. In another form of this older device double-angle testing heads having two angle transducers each, one of which transmits its sonic rays at a right angle to the welded seam (detection of longitudinal defects) and the other sends out its sonic rays at an acute angle to the welded seam (detection of transverse defects) are used. At least four testing heads are required to test for longitudinal and transverse defects from the beginning to the end of the welded seam.

THE INVENTION

It is the principal object of the invention to provide a testing device which requires little space, in which the testing heads can be centrally set and with which a welded seam can be completely and automatically tested from the beginning to the end of the seam.

In accordance with the invention, one longitudinal defect test transducer and two transverse defect test transducers are jointly accommodated on one of two testing aggregates which are arranged on both sides of the welded seam opposite each other. This construction offers the advantage that only one testing aggregate is present on each side of the welded seam which contains the required test transducers for the detection of longitudinal and transverse defects.

Further in accordance with the invention the testing aggregates can be test blocks in which at least the test transducers for the determination of transverse defects are adjustably mounted in their position toward each other and/or in their position to the welding seam. The test transducers can thus be exactly lined up in their optimal position.

In another form of execution of the invention the testing aggregates can be testing heads in which a test transducer for longitudinal defects and two test transducers for transverse defects are installed in a stationary, non-adjustable manner. The stationarily installed test transducers of two testing heads are arranged on two opposite sides of the welded seam. The pairs of test transducers for transverse defects, one element of each pair on each testing head, being arranged on the same side of the test transducers for longitudinal defects and disposed such that their sonic rays hit the seam to be examined at the same spot.

The testing heads are advantageously adjustable in their distance from the welded seam and in their mutual position with respect to each other.

The invention may take physical form in certain parts and arrangements of parts, a preferred embodiment of which will be described in detail in the specification and illustrated in the accompanying drawings which form a part hereof and wherein

PREFERRED EMBODIMENT

Figure 1:
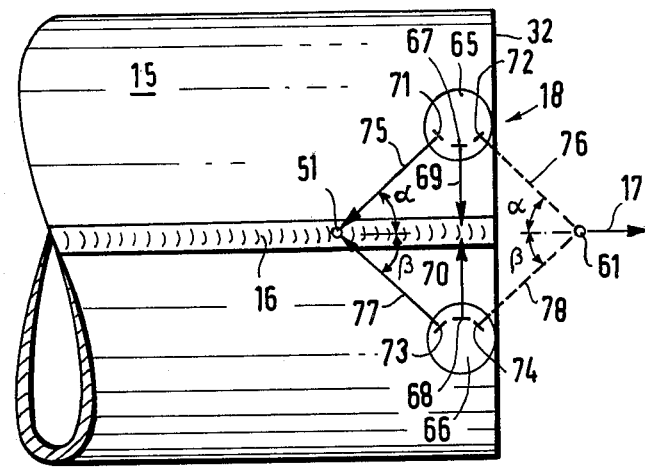
FIG. 1 is a schematic top view of an ultrasonic testing device according to the invention for the examination of the longitudinal welded seam of a tube at the beginning of the tube.

Referring now to the drawings wherein the showings are for purposes of illustrating the preferred embodiment of the invention and not for limiting same, a steel tube 15 which is produced by bending a steel sheet and whose longitudinal welded seam 16 is to be tested for longitudinal and transverse defects is shown. Tube 15 is conducted in the direction of the arrow 17 underneath and past a sonic testing device which is schematically represented in the drawing and designated in its entirety with 18. The testing device 18 has two testing aggregates 65 and 66 which are arranged on opposite sides of the welded seam 16 and are carried by an elevating mechanism not shown here in any detail. The elevating mechanism can be lowered onto the tube 15 when the leading edge 32 of the tube reaches the testing device.

Each of the two testing aggregates 65 and 66 has a stationarily installed test transducer 67 and 68 respectively for longitudinal defects which sends out sonic rays 69 and 70 respectively perpendicularly to the welded seam 16. The testing aggregates 65 and 66 are independently adjustable in longitudinal direction and transversally to the welded seam. The testing aggregates 65 and 66 are aligned in such a way that the test transducers 67 and 68 lie opposite each other, so that they not only receive the sonic rays emitted by them and reflected at the welded seam but also receive the sonic rays emitted for the control of the acoustical contact by the test transducers for longitudinal defects of the testing aggregate arranged on the other side of the welded seam.

On both sides of the test transducers 67 and 68 respectively for longitudinal defects are arranged in each testing aggregate 65 and 66 respectively a pair of test transducers 71 and 72 as well as 73 and 74 respectively for transverse defects. These test transducers for transverse defects stand at an angle to the test transducers 67 and 68 respectively for longitudinal defects, so that their sonic rays 75 and 76 as well as 77 and 78 hit the welded seam 16 at an acute angle α and β respectively at the same points 51 and 61 respectively. The test transducers 71 and 72 respectively can be stationarily installed. Test transducers 71 and 72 can also be adjustably mounted in the testing aggregate 65 or 66. The testing device can then be better adapted to the specific workpiece to be tested and to the welded seam to be tested. On the other hand testing heads with stationarily installed, preadjusted test transducers are easier to handle.

At the beginning of the examination of a welded pipe or tube the test aggregates 65 and 66 are at the leading edge of the tube. The transducers are activated and interrogated in the following repeating sequence of steps, in which the test for longitudinal defects is designated with "L", the test for transverse defects with "Q" and the coupling control with "K".

|         |   | Transmit |       | Receive |
|---------|---|----------|-------|---------|
| Step 1: | L | 68       | ----- | 68      |
| Step 2: | L | 67       | ----- | 67      |
| Step 3: | K | 68       | ----- | 67      |
| Step 4: | K | 67       | ----- | 68      |
| Step 5: | Q | 73       | ----- | 71      |
| Step 6: | Q | 71       | ----- | 73      |

Advance of the tube 15 in the direction of the arrow 17 brings the leading edge 32 to the point 61, where the sonic rays 76 sent out by the test transducer 72 for transverse defects are directed. The sonic rays are reflected at the welded seam and run on to the test transducer 74 of the opposite testing aggregate 66 or vice versa. The area of the welded seam at the beginning of the tube, not tested up to now for transverse defects, can then be examined by the testing transducers 72 and 74 for transverse defects in the following steps:

|         |   | Transmit |       | Receive |
|---------|---|----------|-------|---------|
| Step 7: | Q | 74       | ----- | 72      |
| Step 8: | Q | 72       | ----- | 74      |

Figure 2:
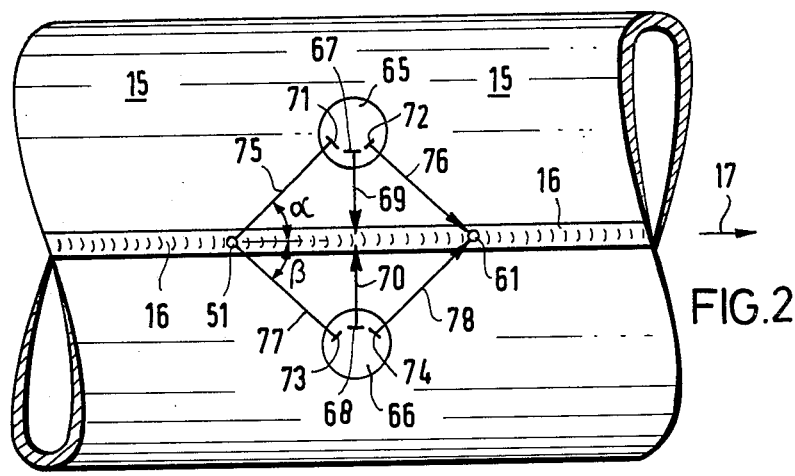
FIG. 2 is a schematic top view of the testing device of FIG. 1 in the center of the tube; and, FIG. 3 is a schematic top view of the testing device of FIG. 1 at the end of the tube.
Figure 3:
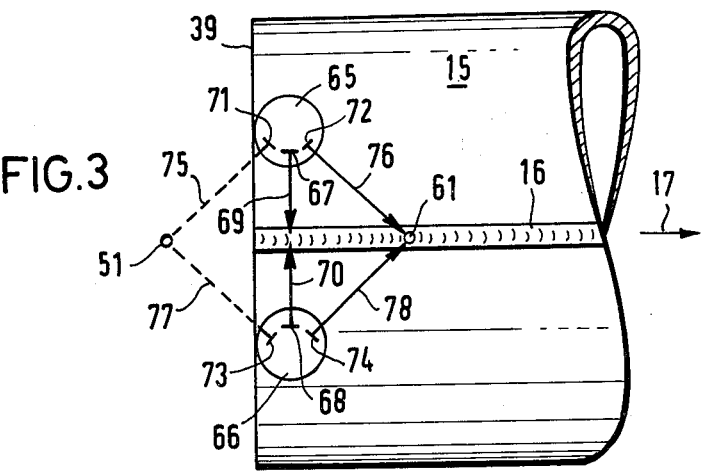

The welded seam in the middle of the tube is tested in the same manner, as it is schematically represented in FIG. 2. It is not necessary to interrogate the testing aggregates in all rhythmic steps indicated above, but the following rhythmic sequence suffices for the complete test:

|         |   | Transmit |       | Receive |
|---------|---|----------|-------|---------|
| Step 1: | L | 68       | ----- | 68      |
| Step 2: | L | 67       | ----- | 67      |
| Step 3: | K | 68       | ----- | 67      |
| Step 4: | Q | 73       | ----- | 71      |
| Step 5: | Q | 74       | ----- | 72      |

As the tube 15 leaves the testing apparatus its trailing edge 39 reaches the point 51. The examination of the welded seam 16 is possible only with the test transducers 67 and 68 for longitudinal defects and the test transducers 72 and 74 for transverse defects. The welded seam has already been tested for transverse defects by the test transducers 71 and 73, so that only a test for longitudinal defects is required until the testing aggregates 65 and 66 are lifted off from the tube.

The invention is not restricted to the example of execution. There are also other forms of execution possible in which the test transducers for the detection of longitudinal and transverse defects are accommodated in one testing aggregate. It is only essential that two testing beams for the detection of transverse defects are directed at an angle to the welding seam in opposite directions toward the beginning and the end of the welding seam which go out from approximately the same point as the sonic rays for the detection of longitudinal defects. Of course, it is possible to carry out the examination in rhythmic sequence other than those indicated above without stepping beyond the framework of the invention.

We claim:

1. An ultrasonic non-destructive testing apparatus for welded seams on tubes comprising: a pair of test transducers for longitudinal defects; first and second pairs of test transducers for transverse defects, each said transverse defect transducer pair having a first element disposed on a first side of said welded seam and a second element disposed on a second side of said welded seam, said first transverse defect transducer pair directing ultrasonic rays at an acute angle to said welded seam intersecting said welded seam at a point on a first side of said longitudinal defect transducer pair, said second transverse defect transducer pair directing ultrasonic rays at an acute angle to said welded seam intersecting said welded seam at a point on a second side of said longitudinal defect transducer pair; and all transducer elements on said first side of said welded seam being mounted close together on a first testing aggregate and all transducer elements on said second side of said welded seam being mounted close together on a second testing aggregate.

2. The apparatus of claim 1 wherein said first testing aggregate and said second testing aggregate are disposed on a single line perpendicular to said welded seam opposite one another.

3. The apparatus of claim 2 wherein said longitudinal defect transducers direct ultrasonic rays at right angles to the welded seam.

4. The apparatus of claim 1, wherein said testing aggregates are testing blocks on which at least said transverse defect test transducer elements are adjustably mounted such that their position and orientations are adjustable.

5. The apparatus of claim 1, wherein the testing aggregates are testing heads in which said longitudinal defect transducer pair and said first and second transverse defect transducer pair elements are stationarily installed.

6. The apparatus of claim 5, wherein said testing heads with the stationarily installed test transducer elements are adjustable in their distance from the welded seam and in their mutual position along the seam with respect to each other.

* * * * *